Feb. 13, 1940. W. KORDES Plant Pat. 362
ROSE PLANT
Filed June 1, 1939
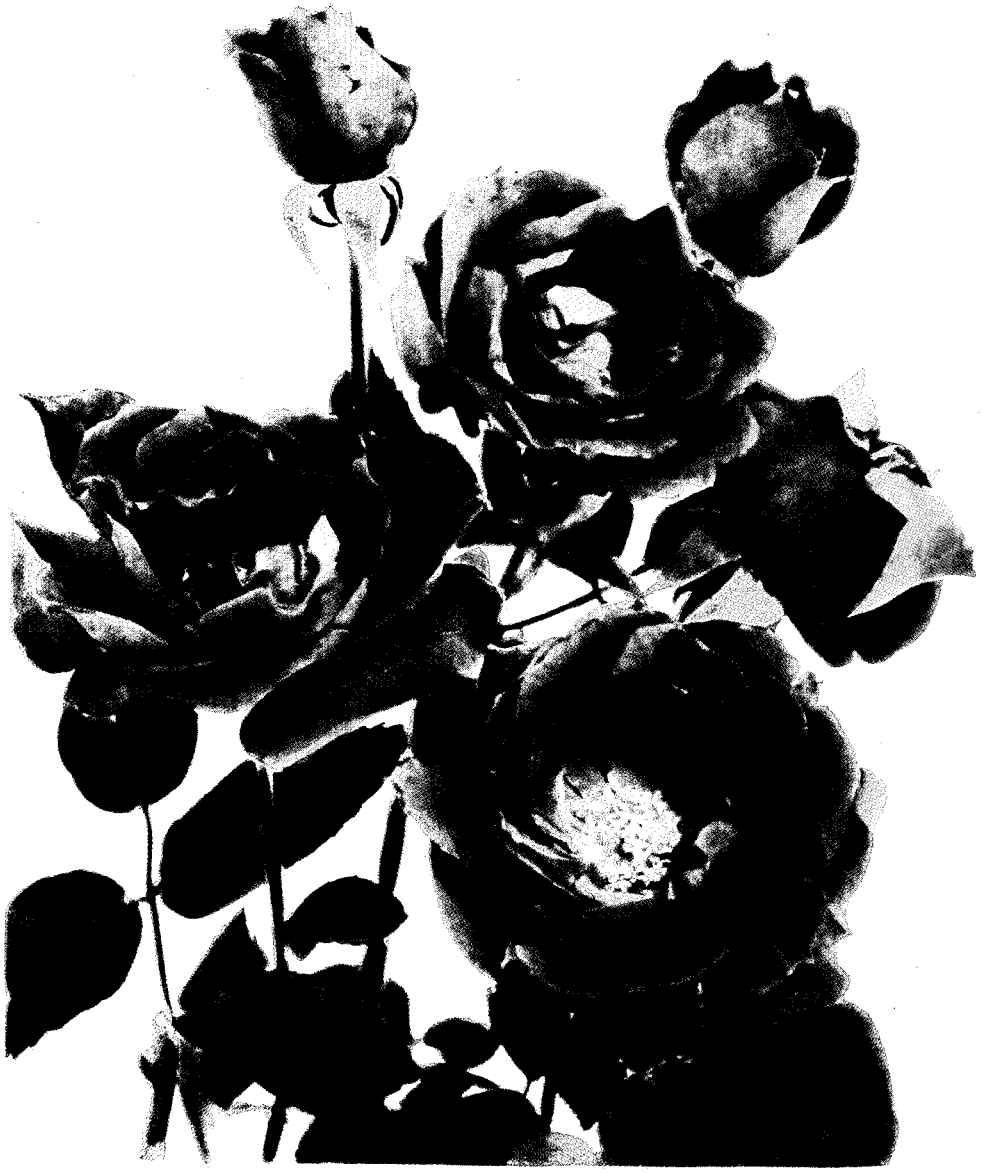
Inventor
W. Kordes
By Robb & Robb
Attorneys Patented Feb. 13, 1940

Plant Pat. 362

UNITED STATES PATENT OFFICE

362

ROSE PLANT

Wilhelm Kordes, Sparrieshoop in Holstein, Germany, assignor to Jackson & Perkins Company, Newark, N. Y.

Application June 1, 1939, Serial No. 276,919

1 Claim. (Cl. 47—61)

The present invention relates to a new and distinct variety of rose plant of the large flowered Polyantha type.

In this class of roses, the new variety possesses many distinctive features producing a rich display, among which may be noted the following as of importance:

(1) The Ox-blood Red color of the bud when the sepals first divide;

(2) The velvety Carmine inside of the petals and shiny Pomegranate Purple outside of the petals when half opened;

(3) The Carmine to Ox-blood Red color on the inside of the petals and Carmine outside petals of the fully opened flower;

(4) The large size of the individual flowers when fully expanded;

(5) The fading from clear Ox-blood Red to Carmine in the second and third days of blooming;

(6) The thick, notched, irregularly arranged petals which last long but drop off cleanly; and (7) The prominent Yellow Ocher anthers and light Jasper Red filaments.

The plant is further marked as distinctive in view of the Madder Brown color on the under side and Maroon color on the upper side of the immature foliage, while the old foliage presents a Dark Cress Green upper side and Light Cress Green under side.

The thorns are few in number, Hessian Brown in color, narrow based and downwardly hooked.

The plant is further notable for the strength of the shoots and the vigor of growth.

Asexual reproduction has shown that the plant comes true to form.

The following is a detailed description of the new variety, the color terminology being in accord with Ridgway's color standard:

Parentage:
*Seed parent.*—Dance of Joy.
*Pollen parent.*—Crimson Glory.
Classification:
*Botanic.*—Large Flowered Polyantha.
*Commercial.*—Floribunda.

*Flower*

Blooming habit:
Observations made in the morning of June 30, 1938, at Newark, New York.
Blooms once.
Recurrent—continuous.
Bud:
*Size.*—Medium.
*Form.*—Urn. Unaffected by wet or hot weather.
*Color.*—When sepals first divide Ox-blood Red, Plate I. When petals begin to unfurl—between Ox-blood Red and Carmine, Plate I. When half blown: inside of petals—Carmine, Plate I; reverse of petals—Pomegranate Purple, Plate 12.
*Sepals.*—Smooth edge. Curl back in early stages as flower opens.
*Calyx.*—Shape—apple. Size—small. Aspect—smooth.
*Peduncle.*—Length — long. Aspect — smooth. Color—Brownish Olive, Plate 30. Strength—erect.
*Opening.*—Bud opens well. Is not affected by adverse conditions.
Bloom:
*Size.*—Medium. Average size when fully expanded—4".
*Borne.*—In irregular clusters.
*Stems.*—Long, strong.
*Form.*—When first open—cupped. Permanence—flattens.
*Petalage.*—Double (full but open center). Number of petals under normal conditions—18.
*Color.*—Center of flower—between Ox-blood Red and Carmine, Plate I. Outer petals—between Carmine and Spectrum Red, Plate I. Base of petals (aiglet)—Pinard Yellow, Plate 4. Inside of petals—between Carmine and Ox-blood Red, Plate I. Reverse of petals—Carmine, Plate I. General tonality from a distance—Scarlet Red.
*Discoloration.*—At end of first day—Ox-blood Red to Carmine, Plate I. Second day—Carmine, Plate I. Third day—Carmine, Plate I.
Petals:
*Texture.*—Thick. Unaffected by wet or hot weather.
*Appearance.*—Inside—velvety. Outside—shiny.
*Form.*—Notched.
*Arrangement.*—Informal (with "rags" in center). Petaloids in center—few, small.
*Persistence.*—Drop off cleanly.
*Lasting quality.*—On the plant—long. As cut flower—fair.
Genital organs:
*Stamens, anthers.*—Large. Color — Yellow Ocher, Plate 15. Arrangement — regular round styles.
*Stamens, filaments (threads).*—Medium length. Color—Light Jasper Red, Plate 13.
*Pollen.*—Zinc Orange, Plate 15.
*Styles.*—Bunched, medium length, heavy.
*Stigmas.*—Color—Pinard Yellow, Plate 4.

*Ovaries.*—All enclosed in calyx.

Fruit:

Variety is fertile with its own pollen.

*Form.*—Depressed top.

*Aspect.*—Smooth.

*Sepals.*—Caducous (soon falling).

*Plant*

Form:

Bush.

Growth:

Vigorous. branching, compact.

Foliage:

*Number of leaflets.*—5 to 7.

*Size.*—Medium.

*Quantity.*—Normal.

*Color.*—New foliage: upper side—Maroon, Plate 1; under side—Madder Brown, Plate 13. Old foliage: upper side—Dark Cress Green, Plate 31; under side—Light Cress Green, Plate 31.

*Shape.*—Oval pointed.

*Texture.*—Upper side—leathery. Under side—rough. Ribs and veins—ordinary.

*Edge.*—Serrated (saw toothed).

*Serration.*—Single, large.

*Rachis.*—Color—Light Cress Green, Plate 31. Under side—smooth.

*Stipules.*—Medium length, bearded.

*Disease resistance.*—Resistant.

Wood:

*New wood.*—Color—Vandyke Red, Plate 13. Bark—rough.

*Old wood.*—Color—Cress Green—Plate 31. Bark—smooth.

Thorns (divided into thorns, prickles and short needles):

*Thorns.*—Quantity: on main stalks from base—few; on laterals from stalk—few. Form—narrow base, medium length, hooked downward. Color when young—Hessian Brown, Plate 13. Position—in pairs.

*Prickles.*—Quantity: on main stalks—few; on laterals—few. Color—Hessian Brown, Plate 13.

*Short needles.*—None.

I claim:

A new and distinct variety of large flowering Polyantha rose plant, characterized as to novelty by the rich coloring of its bud and open flower, its large size, the form and color of petals, the color of foliage, the form and color of thorns, substantially as shown, and the vigor of growth and strength of shoots, as described.

WILHELM KORDES.